(12) United States Patent
Mamiya

(10) Patent No.: US 12,053,402 B2
(45) Date of Patent: Aug. 6, 2024

(54) STENT DELIVERY DEVICE, STENT DELIVERY SYSTEM, AND METHOD

(71) Applicant: OLYMPUS CORPORATION, Tokyo (JP)

(72) Inventor: Tomohiko Mamiya, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 852 days.

(21) Appl. No.: 17/169,935

(22) Filed: Feb. 8, 2021

(65) Prior Publication Data
US 2021/0177631 A1 Jun. 17, 2021

Related U.S. Application Data

(63) Continuation of application No. PCT/JP2018/030195, filed on Aug. 13, 2018.

(51) Int. Cl.
| | |
|---|---|
| *A61F 2/966* | (2013.01) |
| *A61B 17/11* | (2006.01) |
| *A61F 2/90* | (2013.01) |
| *A61F 2/95* | (2013.01) |
| *A61M 27/00* | (2006.01) |

(52) U.S. Cl.
CPC .......... *A61F 2/966* (2013.01); *A61B 17/1114* (2013.01); *A61F 2/90* (2013.01); *A61F 2/9522* (2020.05); *A61M 27/002* (2013.01); *A61B 2017/1139* (2013.01)

(58) Field of Classification Search
CPC .... A61F 2/064; A61F 2/07; A61F 2/90; A61F 2/89; A61F 2/88; A61F 2/86; A61F 2/95; A61F 2002/9505; A61F 2002/9511; A61F 2/966; A61F 2/9522; A61F 2002/045;
(Continued)

(56) References Cited

U.S. PATENT DOCUMENTS

| | | | | |
|---|---|---|---|---|
| 6,478,773 B1 * | 11/2002 | Gandhi | ............ | A61B 17/12136 |
| | | | | 604/113 |
| 2007/0293929 A1 | 12/2007 | Aoba et al. | | |

(Continued)

FOREIGN PATENT DOCUMENTS

| | | | |
|---|---|---|---|
| EP | 1867305 A2 | 12/2007 | |
| EP | 3028680 A1 | 6/2016 | |

(Continued)

OTHER PUBLICATIONS

English translation of JP-2006346350 (Year: 2006).*
International Search Report dated Oct. 9, 2018 issued in PCT/JP2018/030195.

*Primary Examiner* — Mohamed G Gabr
*Assistant Examiner* — Aman Kumar Mann
(74) *Attorney, Agent, or Firm* — Scully, Scott, Murphy & Presser, P.C.

(57) ABSTRACT

For the purpose of placing a stent at a position where the digestive tract wall and the bile duct wall are more reliably brought into close contact, provided is a stent delivery device including an inner shaft having a longitudinal axis and a tubular outer sheath through which the inner shaft is inserted so as to be movable along the longitudinal axis, wherein the inner shaft includes a fixing mechanism that fixes a distal-end section of a stent extended in accordance with relative movement of the inner shaft and the outer sheath, to the inner shaft in a releasable manner.

8 Claims, 9 Drawing Sheets

(58) Field of Classification Search
CPC .............. A61F 2002/9665; A61B 17/11; A61B 17/1114; A61B 2017/1107; A61M 27/002
See application file for complete search history.

(56) References Cited

U.S. PATENT DOCUMENTS

| | | | | |
|---|---|---|---|---|
| 2009/0030497 | A1* | 1/2009 | Metcalf | A61F 2/9662 623/1.1 |
| 2009/0276027 | A1* | 11/2009 | Glynn | A61F 2/95 623/1.13 |
| 2011/0112622 | A1* | 5/2011 | Phan | A61F 2/95 623/1.11 |
| 2011/0137394 | A1 | 6/2011 | Lunsford et al. | |
| 2011/0257720 | A1* | 10/2011 | Peterson | A61F 2/966 623/1.11 |
| 2012/0136426 | A1 | 5/2012 | Phan et al. | |
| 2013/0289703 | A1* | 10/2013 | Kinkade | A61F 2/07 623/1.15 |
| 2014/0236278 | A1 | 8/2014 | Argentine et al. | |
| 2016/0158050 | A1* | 6/2016 | Skelton | A61F 2/9517 623/1.11 |
| 2017/0035426 | A1 | 2/2017 | Phan et al. | |
| 2019/0254674 | A1 | 8/2019 | Phan et al. | |

FOREIGN PATENT DOCUMENTS

| | | | |
|---|---|---|---|
| EP | 3284446 | A1 | 2/2018 |
| JP | 2006-346350 | A | 12/2006 |
| JP | 2006346350 | A * | 12/2006 |
| JP | 2007-330796 | A | 12/2007 |
| JP | 2012-527955 | A | 11/2012 |
| JP | 2014-014722 | A | 1/2014 |
| JP | IP 5535313 | B2 | 7/2014 |
| JP | 2016-511042 | A | 4/2016 |
| JP | 2016-189839 | A | 11/2016 |
| JP | 2017-070512 | A | 4/2017 |
| JP | 2017-079815 | A | 5/2017 |
| WO | WO 2010/138277 | A1 | 12/2010 |
| WO | WO 2014/130235 | A1 | 8/2014 |

* cited by examiner

STENT DELIVERY DEVICE, STENT DELIVERY SYSTEM, AND METHOD

CROSS-REFERENCE TO RELATED APPLICATIONS

This is a continuation of International Application PCT/JP2018/030195, with an international filing date of Aug. 13, 2018, which is hereby incorporated by reference herein in its entirety.

TECHNICAL FIELD

The present invention relates to a stent delivery device, a stent delivery system, and a method.

BACKGROUND ART

There is a known stent delivery device that forms a through-hole penetrating through the stomach wall and bile duct wall and that disposes a stent at a position in the through-hole over the stomach wall and the bile duct wall in order to drain bile from the bile duct into the stomach (for example, see Publication of Japanese Patent No. 5535313.

This stent delivery device frees a stent that has been disposed in a contracted state between an inner shaft and an outer sheath, sequentially from a distal end of the stent, by sliding the outer sheath toward the proximal end with respect to the inner shaft. First, the distal end of the stent is expanded in the bile duct, and then the proximal end of the stent is expanded in the stomach, whereby the stomach wall and the bile duct wall are sandwiched between the expanded distal end and proximal end and are brought into close contact with each other.

SUMMARY OF INVENTION

According to one aspect, the present invention provides a stent delivery device including: an inner shaft that has a longitudinal axis; and a tubular outer sheath through which the inner shaft is inserted so as to be movable along the longitudinal axis, wherein the inner shaft comprises a fixing mechanism that is configured to fix, to the inner shaft in a releasable manner, a distal-end section of a stent extended in accordance with relative movement of the inner shaft and the outer sheath; and the fixing mechanism comprises a thread that is attached to the distal-end section of the stent and a protrusion on which the thread is hooked.

DESCRIPTION OF EMBODIMENT

A stent delivery device 1, a stent delivery system, and a stent delivery method according to one embodiment of the present invention will be described below with reference to the drawings.

The stent delivery system of this embodiment includes the stent delivery device 1 of this embodiment and a stent 6.

Figure 1:
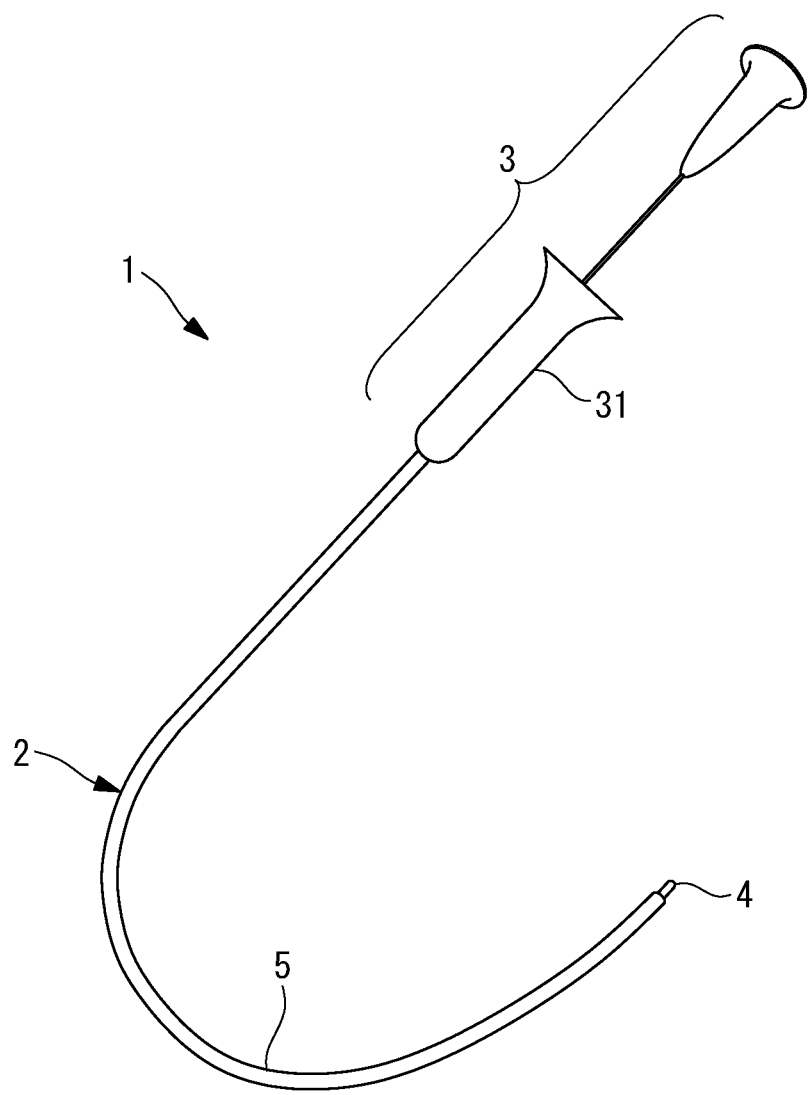
FIG. 1 is a view showing the overall configuration of a stent delivery device according to one embodiment of the present invention.

As shown in FIG. 1, the stent delivery device 1 of this embodiment includes an insertion portion 2 that is inserted through a channel of an endoscope and an operation portion 3 that is connected to a proximal end of the insertion portion 2 and that is operated by an operator.

The insertion portion 2 includes a tubular inner shaft 4 that has a longitudinal axis and a tubular outer sheath 5 through which the inner shaft 4 is inserted so as to be movable in the direction along the longitudinal axis.

The stent 6 is formed of a mesh-like metal material, for example, and in a tubular form having a distal end and a proximal end. The stent 6 can be changed in shape between a contracted state in which it is contracted in radial directions and an extended state in which it is extended in the radial directions. In a free state of being freed from restraint, the stent 6 is extended into a shape in which the outer diameter is larger at the distal end and the proximal end than at the center in the axial direction (at a central area between the distal end and the proximal end of the stent 6). The stent 6 transits from the contracted state to the extended state through relative movement of the inner shaft 4 and the outer sheath 5, i.e., by retraction of the outer sheath 5 with respect to the inner shaft 4.

Figure 2:
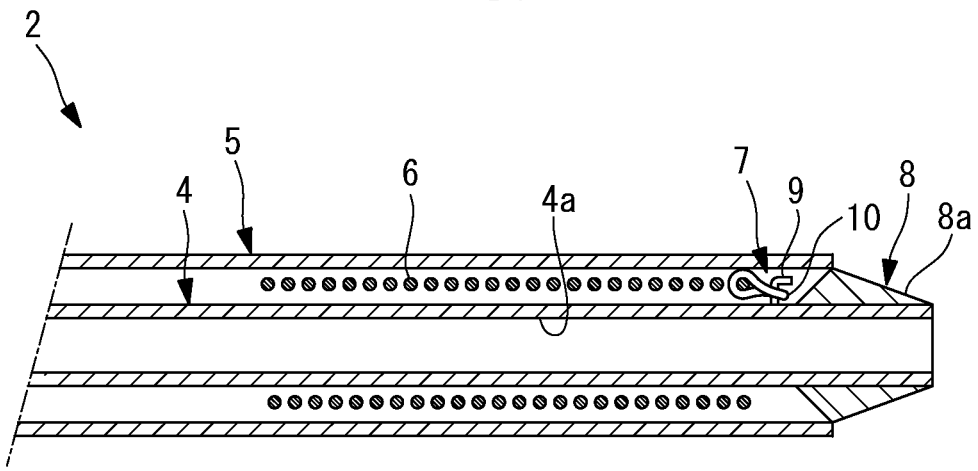
FIG. 2 is a longitudinal sectional view partially showing a distal-end section of an insertion portion of the stent delivery device shown in FIG. 1.

As shown in FIG. 2, the inner shaft 4 includes a fixing mechanism 7 that fixes the distal end of the stent 6 to the inner shaft 4 in a releasable manner. The inner shaft 4 has flexibility and includes an inner hole 4a through which a guide wire (not shown) is inserted over the entire length. The inner shaft 4 has a distal-end tip 8 at a distal end thereof. The distal-end tip 8 has a tapered surface 8a that is tapered toward the distal end of the inner shaft 4. An electrode for performing energization may be provided on the distal-end tip 8.

The outer sheath 5 has flexibility and has an inner diameter fully larger than an outer diameter of the inner shaft 4. When the inner shaft 4 is inserted into the outer sheath 5, a cylindrical gap is formed between an outer circumferential surface of the inner shaft 4 and an inner circumferential surface of the outer sheath 5. When the stent 6 is deformed into the contracted state, the stent 6 turns into a cylindrical form that can be accommodated in the cylindrical gap between the inner shaft 4 and the outer sheath 5.

As shown in FIG. 2, for example, the fixing mechanism 7 includes: a protrusion 9 that is provided at one place, in the circumferential direction, of the outer circumferential surface of the inner shaft 4; and a fixing thread (thread) 10 that is attached to the distal end of the stent 6. Hereinafter, the protrusion 9 is also referred to as a hook 9. The hook 9 has such a form as to extend outward in a radial direction from the outer circumferential surface of the inner shaft 4 and then as to be bent toward the distal end. A gap is provided between a distal end of the hook 9 and a proximal-end surface of the distal-end tip 8 so as to allow the fixing thread 10 to pass therebetween.

The fixing thread 10 is formed in a loop shape such that one end is attached to the distal end of the stent 6, and the other end can be loosely hooked on the hook 9, and the fixing thread 10 is attached to the distal end of the stent 6 by being made to pass between wires of the stent 6. The loop shape of the fixing thread 10 is formed by tying one end and the other end of a single thread. It is preferred that the diameter of the fixing thread 10 be the same level as the diameter of each of the wires of the stent 6.

The operation portion 3 includes a slider 31 that retracts the outer sheath 5 toward the proximal end with respect to the inner shaft 4.

The stent delivery method using the thus-configured stent delivery device 1 of this embodiment will be described below.

In order to supply the stent 6 from the stomach (digestive tract, first lumen) A side to the bile duct wall of the bile duct (second lumen) B by using the stent delivery device 1 of this embodiment, the distal end of an endoscope is inserted into the stomach A, and the distal end of the endoscope is disposed at an inner-surface position on the stomach wall of the stomach A that is opposed to the bile duct wall, through observation with the endoscope. In this state, a needle (not shown) is made to protrude from the distal end of the endoscope through the channel of the endoscope and is inserted from the inner surface of the stomach wall into the bile duct B. A guide wire that is guided through an inner hole of the needle is placed in position, the needle is pulled out, and, instead of the needle, the insertion portion 2 of the stent delivery device 1 is guided into the channel of the endoscope.

Figure 3:
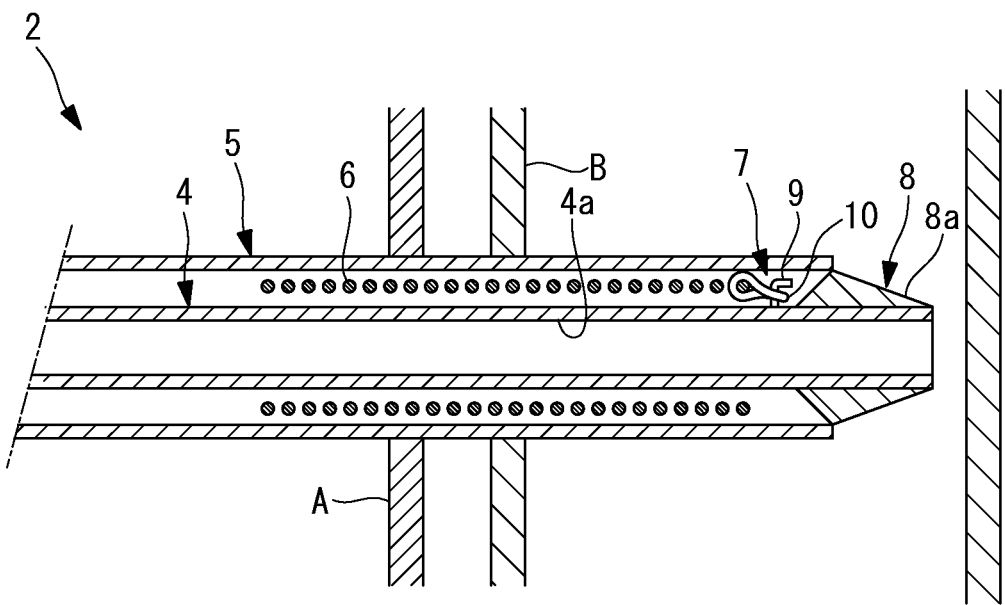
FIG. 3 is a longitudinal sectional view showing a state in which the distal-end section of the insertion portion shown in FIG. 2 is inserted into the bile duct from the digestive tract side.

At this time, the insertion portion 2 is in a state in which only the distal-end tip 8 is exposed from the distal end of the outer sheath 5 and in which the stent 6 in the contracted state is accommodated in the cylindrical gap between the inner shaft 4 and the outer sheath 5. Because the distal-end tip 8 has the tapered surface 8a, which is tapered toward the distal end, the insertion portion 2 of the stent delivery device 1 is pressed toward the distal end by using the guide wire as a guide, thereby making it possible to insert the distal end of the insertion portion 2 into the bile duct B while a hole made by the needle is expanded by the tapered surface 8a, as shown in FIG. 3.

Figure 4:
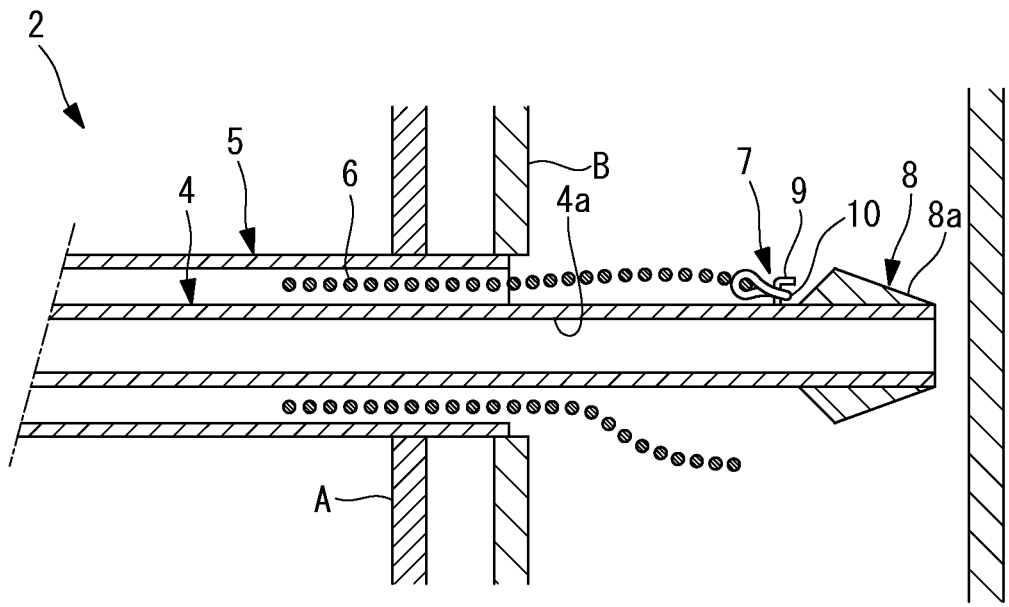
FIG. 4 is a longitudinal sectional view showing a state in which an outer sheath is slightly retracted from the state of FIG. 3.

In this state, when the slider 31 of the operation portion 3 is operated at the outside of the body of a patient to retract the outer sheath 5 with respect to the inner shaft 4, as shown in FIG. 4, at the distal end of the insertion portion 2, the distal end of the outer sheath 5 is pulled out from the bile duct B while the distal end of the inner shaft 4 remains in the bile duct B. Accordingly, the stent 6 accommodated between the inner shaft 4 and the outer sheath 5 is exposed from the distal end, thus being freed from the restrained state.

At this time, when the stent 6 is freed from the state of being restrained from radially outside by the outer sheath 5, the freed distal-end section thereof is likely to transit to the extended state; however, because the distal end of the stent 6 is restrained to the distal end of the inner shaft 4 by the fixing thread 10, the distal end of the stent 6 is held in such a state as not to move toward the proximal end.

Because the fixing thread 10 fixes the stent 6 at one place in the circumferential direction, the other sections of the stent 6 start to extend.

Figure 5:
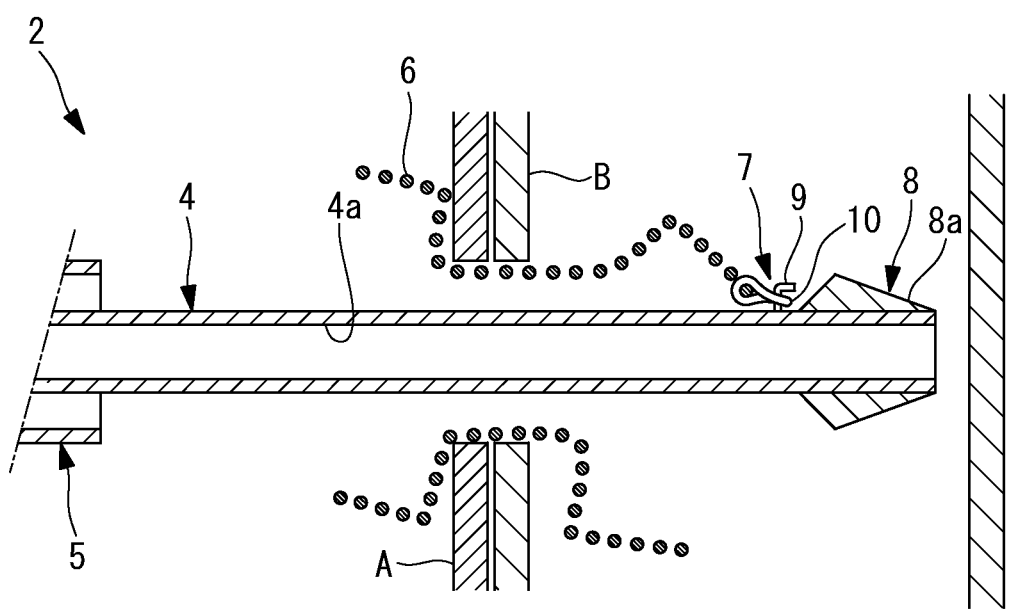
FIG. 5 is a longitudinal sectional view showing a state in which the outer sheath is further retracted from the state of FIG. 4.

When the distal-end section of the stent 6 disposed in the bile duct B extends, the stent 6 turns into a form in which the stent 6 does not easily come off from the bile duct B. Then, as shown in FIG. 5, when the outer sheath 5 is fully retracted with respect to the inner shaft 4, the stent 6 is completely exposed, and the proximal end of the stent 6 also assumes the extended state. When the proximal-end section of the stent 6 disposed in the stomach A extends, the stent 6 turns into a form in which both ends that have assumed the extended state sandwich the stomach wall and the bile duct wall in the thickness direction.

Figure 6:
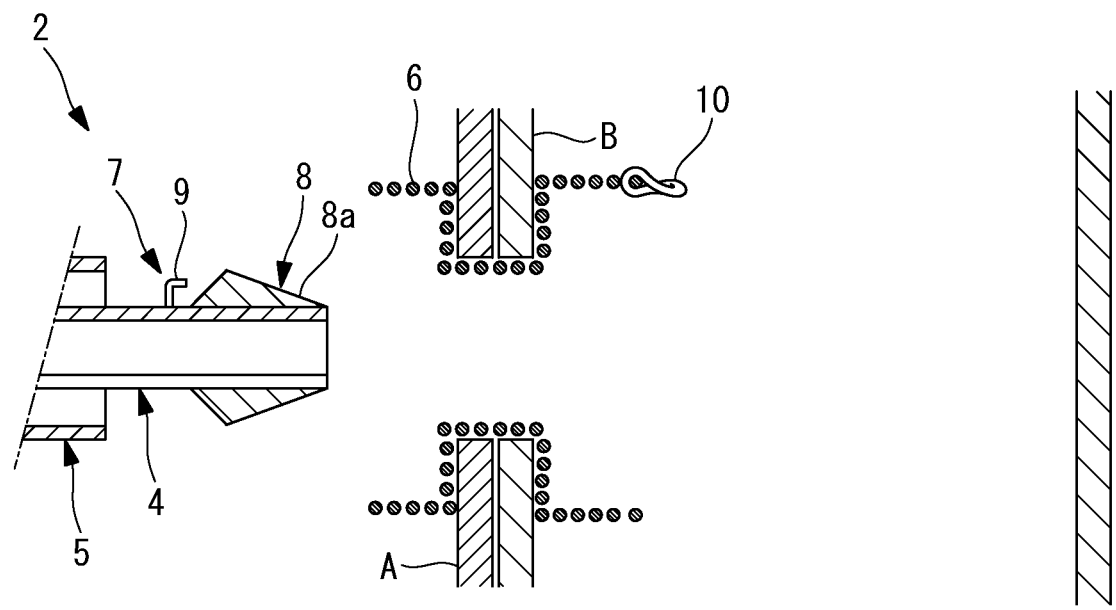
FIG. 6 is a longitudinal sectional view showing a state in which an inner shaft is retracted from the state in FIG. 5 and is pulled out from the bile duct to the digestive tract.

Thereafter, the operation portion 3 is moved toward the proximal end, to retract the inner shaft 4 toward the proximal end, as shown in FIG. 6. Regarding the fixing thread 10, which is attached to the distal end of the stent 6, because one end of the loop shape thereof is hooked on the hook 9 on the inner shaft 4, and the hook 9 is bent toward the distal end, when the inner shaft 4 is moved toward the proximal end, the one end of the loop shape easily comes off from the hook 9, whereby the fixed state of the stent 6 obtained by the fixing mechanism 7 is released. Accordingly, the distal-end section of the stent 6 completely assumes the extended state, and the inner shaft 4 can be pulled out from the inside of the stent 6.

In this way, according to the stent delivery device 1, the stent delivery system, and the stent delivery method of this embodiment, when extension of the stent 6 is started, the distal end of the stent 6 is fixed to the inner shaft 4, thereby making it possible to reliably hold the distal end of the stent 6 inside the bile duct B. Just by moving the inner shaft 4 toward the proximal end with respect to the stent 6, the fixed state obtained by the fixing mechanism 7 is easily released, thus making it possible to pull out the inner shaft 4 from the stent 6. Accordingly, there is an advantage in that it is possible to place the stent 6 inside the body in such a form as to more reliably sandwich the stomach wall and the bile duct wall in the thickness direction.

Figure 7:
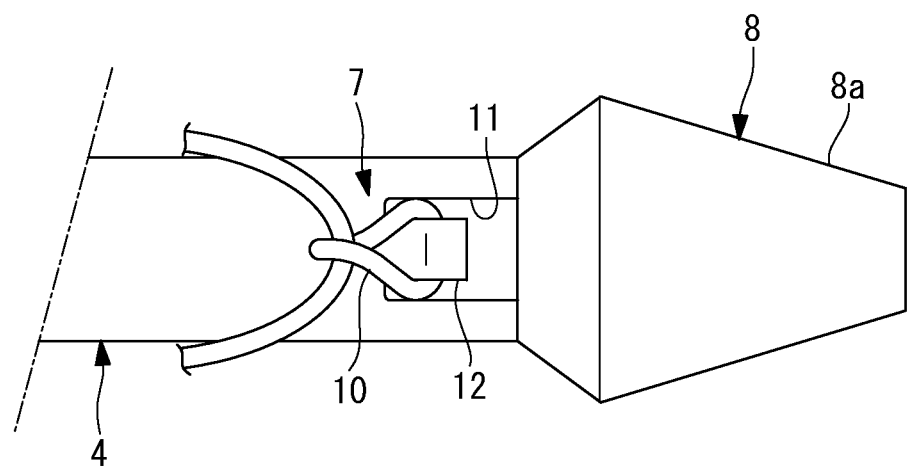
FIG. 7 is a front view showing another example of a fixing mechanism of the stent delivery device shown in FIG. 1.

In this embodiment, although the hook 9, which extends radially outward from the outer circumferential surface of the inner shaft 4 and is then bent toward the distal end of the inner shaft 4, has been illustrated as the fixing mechanism 7, instead of this, as shown in FIG. 7, it is also possible to adopt a protrusion 12 that is provided in a through-hole 11 penetrating the tube wall of the inner shaft 4 in a radial direction and on which one end of the loop-shaped fixing thread 10 is hooked. In this case, the protrusion 12 extends from a proximal end of the periphery of the through-hole 11, which is provided in the outer surface of the inner shaft 4, toward the distal end of the inner shaft 4, so that there is no projection on the outer surface of the inner shaft 4, and it is difficult for the stent 6 to become hooked on the protrusion 12 when the stent 6 extends, whereby the operability is improved.

Figure 8:
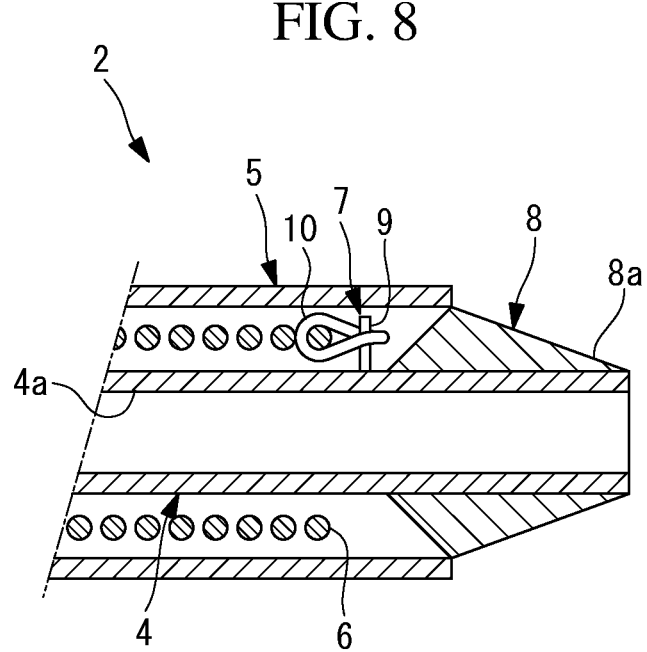
FIG. 8 is a longitudinal sectional view showing still another example of the fixing mechanism of the stent delivery device shown in FIG. 1.
Figure 9:
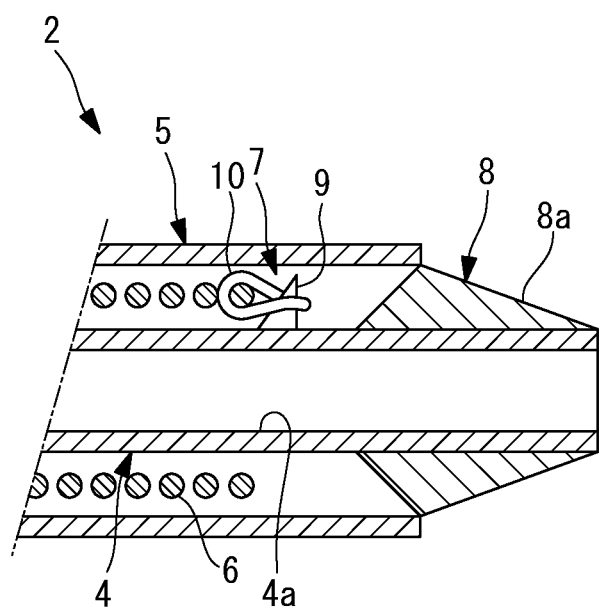
FIG. 9 is a longitudinal sectional view showing still another example of the fixing mechanism of the stent delivery device shown in FIG. 1.

In this embodiment, although the hook form, which extends radially outward from the outer circumferential surface of the inner shaft 4 and is then bent toward the distal end, has been illustrated as a shape of the protrusion 9, instead of this, an arbitrary shape can be adopted. For example, it is also possible to adopt a shape that just extends radially outward from the outer circumferential surface of the inner shaft 4, as shown in FIG. 8, or to adopt a conical shape that extends radially outward from the outer circumferential surface of the inner shaft 4, as shown in FIG. 9. In a case in which a conical protrusion 9 is adopted, it is preferred that the angle between an outer surface of the protrusion 9 close to the distal end of the inner shaft 4 and the outer surface of the inner shaft 4 be 90° or less.

Figure 10:
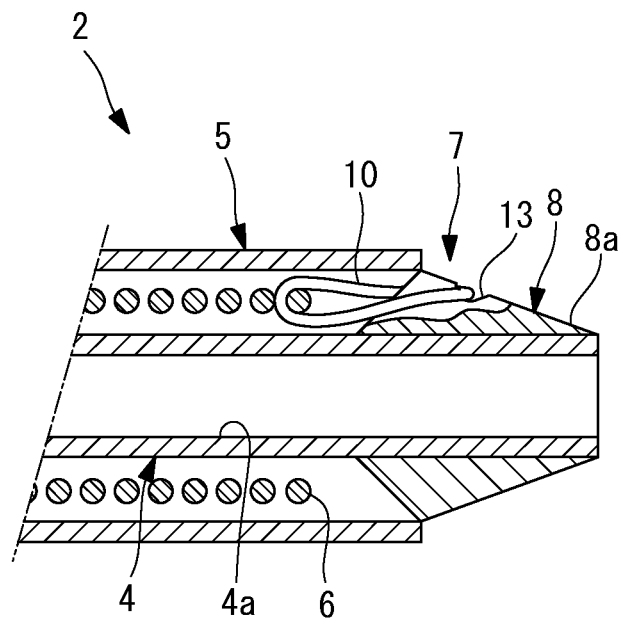
FIG. 10 is a longitudinal sectional view showing still another example of the fixing mechanism of the stent delivery device shown in FIG. 1.
Figure 11:
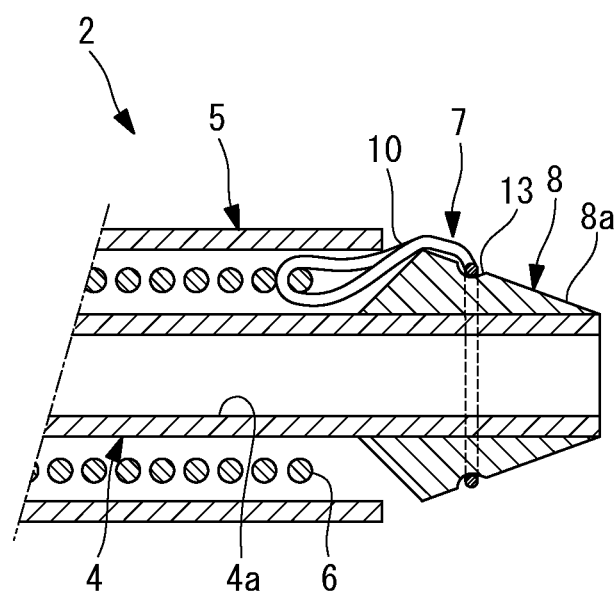
FIG. 11 is a longitudinal sectional view showing still another example of the fixing mechanism of the stent delivery device shown in FIG. 1.

Instead of hooking the fixing thread 10 on the protrusion 9, it is also possible to hook the fixing thread 10 on the distal-end tip 8, as shown in FIG. 10 or 11. In this case, the distal-end tip 8 extends radially outward from the outer circumferential surface of the inner shaft 4, like the protrusion 9, and a depression 13 on which the fixing thread 10 is hooked is provided in the tapered surface 8a of the distal-end tip 8, whereby the distal-end tip 8 functions as a hook, like the protrusion 9. By hooking the fixing thread 10 on the depression 13, it is possible to suppress movement of the stent 6 along the longitudinal axis toward the proximal end of the stent 6 with respect to the inner shaft 4 and to allow relative movement of the stent 6 toward the distal end of the stent 6 with respect to the inner shaft 4, as in the structure in which the fixing thread 10 is hooked on the protrusion 9.

Figure 12:
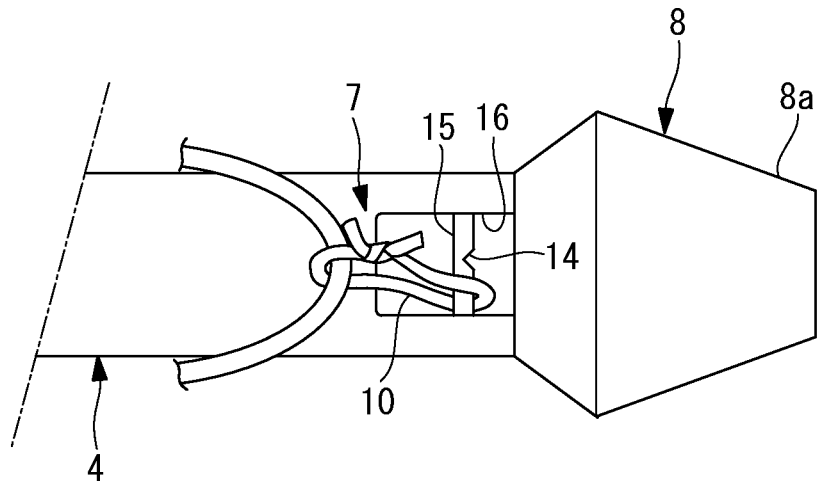
FIG. 12 is a front view showing still another example of the fixing mechanism of the stent delivery device shown in FIG. 1.

Instead of the protrusion 9, which has such a shape as to allow the fixing thread 10 to be easily pulled out by moving the inner shaft 4 toward the proximal end with respect to the stent 6, as shown in FIG. 12, the fixing thread 10 may also be hooked on a stick-like member (protrusion) 15 having a weak section 14 that is easily broken due to a pulling force for moving the inner shaft 4 toward the proximal end. The stick-like member 15 is broken at the position of the weak section 14 by pulling the inner shaft 4, thus allowing the fixing thread 10 to be removed from the stick-like member 15.

Figure 13:
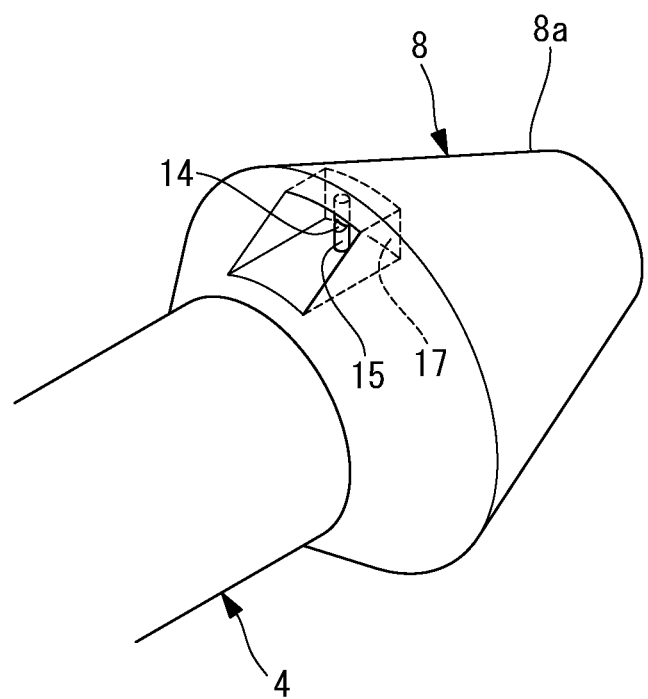
FIG. 13 is a perspective view showing still another example of the fixing mechanism of the stent delivery device shown in FIG. 1.

The stick-like member 15, which has the aforementioned weakness, may be provided in a through-hole 16 provided in the inner shaft 4, so as to extend in a direction intersecting the penetration direction of the through-hole 16, as shown in FIG. 12, or may be provided in a recessed section 17 of the distal-end tip 8, as shown in FIG. 13.

In this embodiment, although a case in which the inner shaft 4 is moved toward the proximal end with respect to the stent 6 has been illustrated as a method for releasing the fixed state obtained by the fixing mechanism 7, instead of this, it is also possible to cut a section of the loop-shaped fixing thread 10 hooked on the inner shaft 4, by using a cutter that is movable inside the inner shaft 4.

In this embodiment, although a case in which the stomach wall and the bile duct wall are brought into close contact has been illustrated, instead of this, the present invention may also be applied to a case in which another digestive tract, such as the duodenum, and the bile duct wall, gallbladder, or a pancreatic cyst are brought into close contact.

Figure 14:
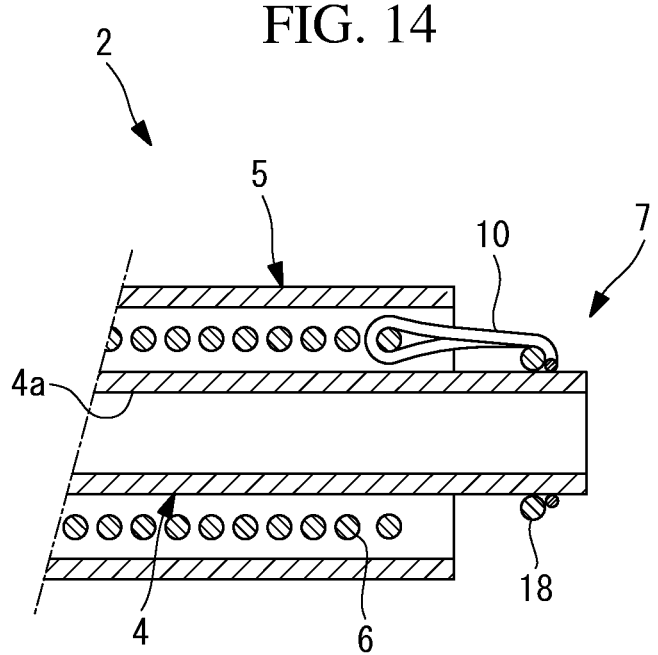
FIG. 14 is a longitudinal sectional view showing still another example of the fixing mechanism of the stent delivery device shown in FIG. 1.

In this embodiment, although the inner shaft 4 that has the distal-end tip 8 provided at the distal end of the inner shaft 4 has been illustrated, instead of this, it is also possible to adopt an inner shaft 4 that does not include the distal-end tip 8. In this case, as shown in FIG. 14, it is also possible to adopt, as the fixing mechanism 7, an attachment member (for example, O-ring) 18 that is attached to the outer surface of the inner shaft 4 in the entire circumferential direction at a position between the distal end of the stent 6 and the distal end of the inner shaft 4. In this case, the attachment member 18 is fixed to the inner shaft 4 by adhesive etc. The loop-shaped fixing thread 10 is put on the distal end of the inner shaft 4 and is hooked on the attachment member 18, thereby being fixed. It is preferred that a dimension of the attachment member 18 from the outer surface of the inner shaft 4 to the farthest position of the attachment member 18 protruded radially outward be the same as the diameter dimension of the fixing thread 10.

Although the attachment member 18 has been described as a projecting part extending in the entire circumferential direction of the inner shaft 4, instead of this, it is also possible to provide a protrusion that is formed on the outer surface of the inner shaft 4 over the entire circumferential direction at a position between the distal end of the stent 6 and the distal end of the inner shaft 4.

Figure 15:
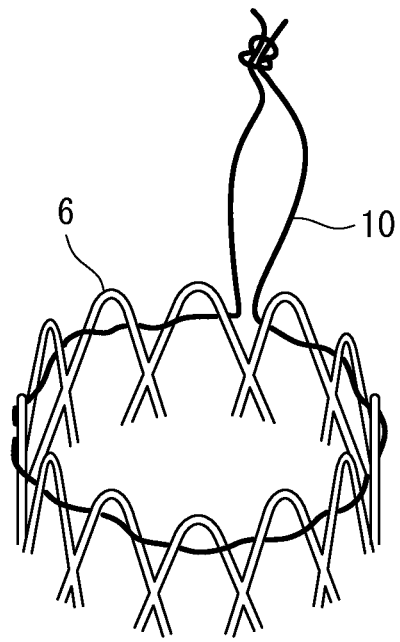
FIG. 15 is a perspective view showing still another example of the fixing mechanism of the stent delivery device shown in FIG. 1.

In this embodiment, although the fixing thread 10 of the fixing mechanism 7 that is fixed to one place of the stent 6 in the circumferential direction has been illustrated, instead of this, as shown in FIG. 15, the fixing thread 10 may be fixed to the stent 6 by being made to pass between the wires of the stent 6, over the entire circumference of the stent 6 or at a plurality of places of the stent 6 in the circumferential direction.

Figure 16:
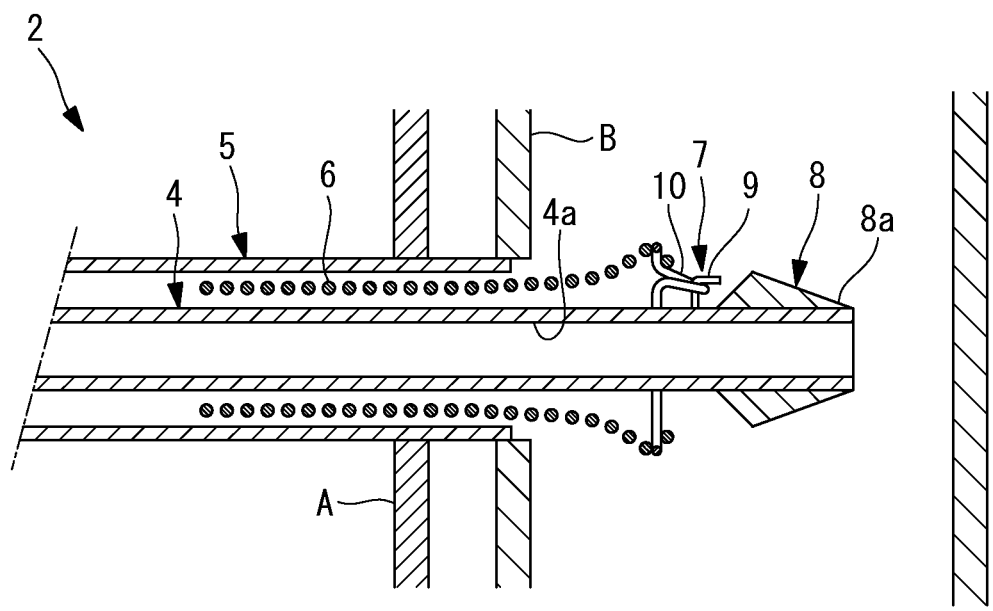
FIG. 16 is a longitudinal sectional view showing still another example of the fixing mechanism of the stent delivery device shown in FIG. 1.

In a case in which the fixing thread 10 is fixed to the entire circumference of the stent 6, as shown in FIG. 16, when the outer sheath 5 is pulled toward the proximal end with respect to the inner shaft 4 to extend the stent 6, the stent 6 transits from the contracted state to the extended state to expand the diameter, while the rear end of the stent 6 is moved toward the distal end. In this case, because the fixing thread 10 is attached to the entire circumference of the distal-end section of the stent 6, the stent 6 assumes a state in which the entire circumference of the distal-end section of the stent 6 is fixed to the inner shaft 4, whereby it is difficult for the stent 6 to tilt with respect to the inner shaft 4, compared with the case in which the fixing thread 10 is fixed to one place on the distal-end section of the stent 6.

Figure 17:
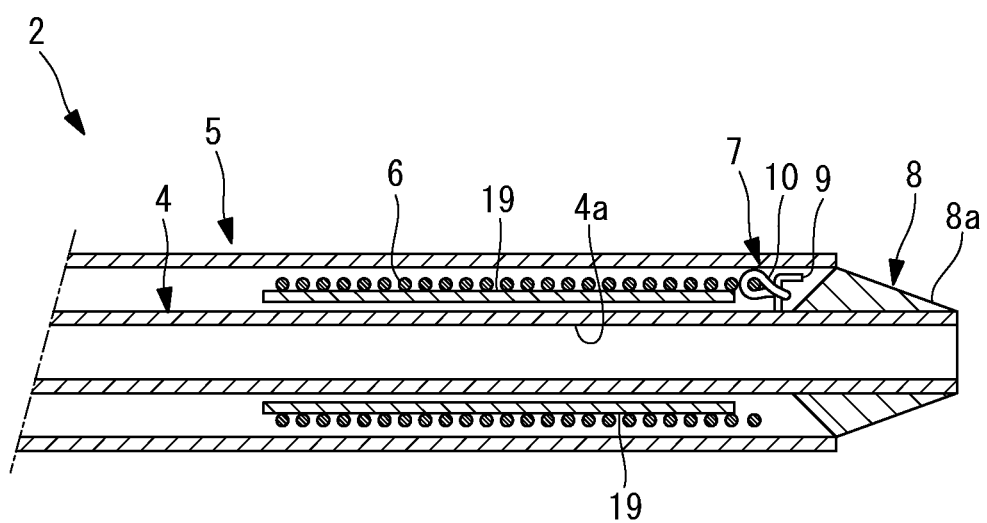
FIG. 17 is a longitudinal sectional view showing still another example of the fixing mechanism of the stent delivery device shown in FIG. 1.

In this embodiment, as shown in FIG. 17, a cover 19 that is formed of a resin tube may be provided inside the stent 6. The cover 19 is fixed to an inner side of the stent 6. Accordingly, in a case in which the tube wall of the first lumen (duodenum or stomach) A and the tube wall of the second lumen (bile duct, gallbladder, or pancreatic cyst) B are brought into close contact, it is possible to discharge a liquid (bile etc.) from the second lumen B toward the first lumen A through the cover 19.

In this embodiment, although the loop shape of the fixing thread 10 formed by tying one end and the other end of the thread has been illustrated, it is also possible to form a loop shape by another method, e.g., bonding of the ends of the thread.

In this embodiment, although a description has been given of an example case in which the fixing thread 10 is fixed to the distal end of the stent 6, instead of this, the fixing thread 10 may be detachably attached to the distal end of the stent 6.

In this embodiment, although the stent 6 that is extended, in the extended state, so as to have a shape in which the outer diameter becomes larger at the distal end and the proximal end than at the center in the axial direction is adopted, the stent 6 is not limited thereto. For example, it is possible to adopt a stent 6 that has the same outer diameter from the proximal end of the stent 6 to the distal end thereof in the extended state. In this case, when the stent 6 is extended in a state in which the central section of the stent 6 has been made to pass through the tube wall, the central section of the stent 6 comes into contact with the tube wall, and pressure is applied to the central section radially inward from the tube wall that is in contact therewith. Accordingly, in the extended state, the outer diameter of the stent 6 becomes larger at the distal end and the proximal end than at the central section. As a result, as in the above-described embodiment, the tube wall of the first lumen A and the tube wall of the second lumen B can be brought into close contact with each other between the distal end and the proximal end of the stent 6.

As a result, the following aspect is read from the above described embodiment of the present invention.

According to one aspect, the present invention provides a stent delivery device including: an inner shaft that has a longitudinal axis; and a tubular outer sheath through which the inner shaft is inserted so as to be movable along the longitudinal axis, wherein the inner shaft comprises a fixing mechanism that is configured to fix, to the inner shaft in a releasable manner, a distal-end section of a stent extended in accordance with relative movement of the inner shaft and the outer sheath; and the fixing mechanism comprises a thread that is attached to the distal-end section of the stent and a protrusion on which the thread is hooked.

According to this aspect, in a state in which the distal-end sections of the inner shaft and the outer sheath have been inserted from the digestive tract side through the digestive tract wall and the bile duct wall and have been disposed in the bile duct side, the outer sheath is relatively moved toward the proximal end with respect to the inner shaft, whereby the stent is freed from the distal end thereof and is extended in radial directions. In this case, although the stent is likely to move toward the proximal end, when extended, due to the elastic restoring force, because the distal-end section of the stent is fixed to the inner shaft by means of the fixing mechanism, the distal-end section of the stent is kept still without moving toward the proximal end.

Specifically, because the distal-end section of the stent does not move toward the proximal end with respect to the inner shaft that has been inserted into the bile duct, the distal-end section of the stent is kept inside the bile duct. Then, in a state in which the stent has been freed over the entire length and in which a section thereof disposed inside the digestive tract has been extended, the fixed state obtained by the fixing mechanism is released, thereby making it possible to extend the stent also in the bile duct and to place the stent at a position where the digestive tract wall and the bile duct wall are more reliably brought into close contact.

In the above-described aspect, the stent may have, in an extended state, a shape in which the diameter becomes larger in the distal-end section and a proximal-end section than in a central area between a distal end of the stent and a proximal end of the stent.

With this configuration, the digestive tract wall and the bile duct wall can be sandwiched and brought into close contact with each other between the distal end and the proximal end, which have large diameters in the extended state.

In the above-described aspect, the fixing mechanism may include a structure in which, at at least a circumferential section of the stent, the distal-end section of the stent is fixed to the inner shaft, the structure suppressing movement of the stent toward the proximal end of the stent along the longitudinal axis with respect to the inner shaft and allowing relative movement of the stent toward the distal end with respect to the inner shaft.

With this configuration, when the freed distal-end section of the stent is extended, movement toward the proximal end is prevented by the fixing mechanism. By just moving the inner shaft toward the proximal end with respect to the stent, the fixed state obtained by the fixing mechanism can be easily released.

In the above-described aspect, the protrusion may be provided at a distal-end section of the inner shaft; and at least a section of the protrusion may extend in the direction from a proximal end of the inner shaft toward a distal end thereof.

With this configuration, when the freed distal-end section of the stent is extended, movement toward the proximal end is prevented by the thread hooked on the protrusion. Just by moving the inner shaft toward the proximal end with respect to the stent, the thread is unhooked from the protrusion, thus making it possible to easily release the fixed state of the stent.

In the above-described aspect, the inner shaft may have, at the distal-end section of the inner shaft, a through-hole that penetrates a tube wall thereof in a radial direction; and the protrusion may extend from a proximal end of the periphery of the through-hole toward the distal end of the inner shaft.

In the above-described aspect, the thread, which has been attached to the distal-end section of the stent, may be fixed to the inner shaft by being hooked on the protrusion; and the inner shaft may be moved toward the proximal end with respect to the stent, whereby the fixed state between the thread and the protrusion is released.

In the above-described aspect, the inner shaft may have a through-hole that penetrates a tube wall of the inner shaft in a radial direction; and the protrusion may be provided in the through-hole so as to extend in a direction intersecting the penetration direction of the through-hole and may have such weakness as to be broken due to an external force applied to the thread.

With this configuration, when the freed distal-end section of the stent is extended, movement toward the proximal end is prevented by the thread hooked on the protrusion provided in the through-hole. If an external force is applied to the protrusion when the inner shaft is moved toward the proximal end with respect to the stent, the protrusion is broken, thereby unhooking the thread from the protrusion and making it possible to easily release the fixed state of the stent.

In the above-described aspect, the thread, which has been attached to the distal-end section of the stent, may be fixed to the inner shaft by being hooked on the protrusion, which is provided in the through-hole of the inner shaft and which has said weakness; and the protrusion may be broken due to a force for moving the inner shaft toward the proximal end with respect to the stent, whereby the fixed state between the thread and the protrusion is released.

In the above-described aspect, the inner shaft may further include a distal-end tip that is provided at the distal end of the inner shaft and that has a tapered surface tapered toward the distal end of the inner shaft; and the fixing mechanism may include the thread, which is attached to the distal-end section of the stent, and a depression that is provided in the tapered surface of the distal-end tip and on which the thread is hooked.

With this configuration, when the freed distal-end section of the stent is extended, movement toward the proximal end is prevented by the thread hooked on the depression on the tapered surface. By just moving the inner shaft toward the proximal end with respect to the stent, the thread is unhooked from the depression on the tapered surface, thus making it possible to easily release the fixed state of the stent.

According to another aspect, the present invention provides a stent delivery system including: an inner shaft that has a longitudinal axis; a tubular outer sheath through which the inner shaft is inserted so as to be movable along the longitudinal axis; and a stent that is configured to be extended in accordance with relative movement of the inner shaft and the outer sheath, wherein the inner shaft comprises a fixing mechanism that is configured to fix a distal-end section of the stent to the inner shaft in a releasable manner; and the fixing mechanism comprises a thread that is attached to the distal-end section of the stent and a protrusion on which the thread is hooked.

According to still another aspect, the present invention provides a stent delivery method including: inserting, from a first lumen into a second lumen together with an inner shaft that has a longitudinal axis and a tubular outer sheath through which the inner shaft is inserted so as to be movable in the direction along the longitudinal axis, a stent having a distal end and a proximal end, in such a state that the stent in a radially contracted form is held in a cylindrical gap between the inner shaft and the outer sheath and that a distal-end section of the stent is fixed to the inner shaft; exposing the entire stent from the outer sheath, while maintaining the state in which the distal-end section of the stent is fixed to the inner shaft, by moving the outer sheath toward the proximal end with respect to the inner shaft and the stent; and releasing the fixed state between the distal-end section of the stent and the inner shaft by moving the inner shaft toward the proximal end with respect to the stent.

The above-described aspect may further include fixing a thread that is attached to the distal-end section of the stent to the inner shaft by hooking the thread on a protrusion that opens toward the distal end of the inner shaft.

The above-described aspect may further include: fixing a thread that is attached to the distal-end section of the stent to the inner shaft by hooking the thread on a protrusion that is provided on the inner shaft and that has weakness; and releasing the fixed state between the thread and the protrusion by breaking the protrusion due to a force for moving the inner shaft toward the proximal end with respect to the stent.

The above-described aspect may further include: fixing a thread that is attached to the distal-end section of the stent to the inner shaft; and releasing the fixed state between the thread and the inner shaft by cutting the thread before the inner shaft is moved toward the proximal end with respect to the stent.

REFERENCE SIGNS LIST

1 stent delivery device
4 inner shaft
5 outer sheath
6 stent
7 fixing mechanism
9 hook (protrusion)
10 fixing thread (thread)
11 through-hole
15 stick-like member (protrusion)
16 through-hole
A stomach (digestive tract, first lumen)
B bile duct (second lumen)

The invention claimed is:

1. A stent delivery device comprising:
   an inner shaft that has a longitudinal axis; and
   a tubular outer sheath through which the inner shaft is inserted so as to be movable along the longitudinal axis,
   wherein the inner shaft comprises a fixing mechanism that is configured to fix, to the inner shaft in a releasable manner, a distal-end section of a stent extended in accordance with relative movement of the inner shaft and the outer sheath;
   the fixing mechanism comprises a thread that is attached to the distal-end section of the stent and a protrusion on which the thread is hooked;
   the protrusion is provided at a distal-end section of the inner shaft;
   at least a section of the protrusion extends in the direction from a proximal end of the inner shaft toward a distal end thereof;
   the inner shaft has, at the distal-end section of the inner shaft, a through-hole that penetrates a tube wall thereof in a radial direction; and
   the protrusion extends from a proximal end of the periphery of the through-hole toward the distal end of the inner shaft.

2. A stent delivery device according to claim 1, wherein the stent has, in an extended state, a shape in which the diameter becomes larger in the distal-end section and a proximal-end section than in a central area between a distal end of the stent and a proximal end of the stent.

3. A stent delivery device according to claim 1, wherein the fixing mechanism comprises a structure in which, at least a circumferential section of the stent at the distal-end section of the stent is fixed to the inner shaft, the structure suppressing movement of the stent toward the proximal end of the stent along the longitudinal axis with respect to the inner shaft and allowing relative movement of the stent toward the distal end with respect to the inner shaft.

4. A stent delivery device according to claim 1,
   wherein the thread, which has been attached to the distal-end section of the stent, is fixed to the inner shaft by being hooked on the protrusion; and
   the inner shaft is moved toward the proximal end with respect to the stent, whereby the fixed state between the thread and the protrusion is released.

5. A stent delivery system comprising:
   an inner shaft that has a longitudinal axis;
   a tubular outer sheath through which the inner shaft is inserted so as to be movable along the longitudinal axis; and
   a stent that is configured to be extended in accordance with relative movement of the inner shaft and the outer sheath,
   wherein the inner shaft comprises a fixing mechanism that is configured to fix a distal-end section of the stent to the inner shaft in a releasable manner;
   the fixing mechanism comprises a thread that is attached to the distal-end section of the stent and a protrusion on which the thread is hooked;
   the protrusion is provided at a distal-end section of the inner shaft;

at least a section of the protrusion extends in the direction from a proximal end of the inner shaft toward a distal end thereof;

the inner shaft has, at the distal-end section of the inner shaft, a through-hole that penetrates a tube wall thereof in a radial direction; and the protrusion extends from a proximal end of the periphery of the through-hole toward the distal end of the inner shaft.

6. A stent delivery method comprising:

inserting, from a first lumen into a second lumen together with an inner shaft that has a longitudinal axis and a tubular outer sheath through which the inner shaft is inserted so as to be movable in the direction along the longitudinal axis, a stent having a distal end and a proximal end, in such a state that the stent in a radially contracted form is held in a cylindrical gap between the inner shaft and the outer sheath and that a distal-end section of the stent is fixed to the inner shaft by fixing a thread that is attached to the distal-end section of the stent to the inner shaft by hooking the thread on a protrusion that is provided on the inner shaft and that has weakness;

exposing the entire stent from the outer sheath, while maintaining the state in which the distal-end section of the stent is fixed to the inner shaft, by moving the outer sheath toward the proximal end with respect to the inner shaft and the stent; and releasing the fixed state between the distal-end section of the stent and the inner shaft by moving the inner shaft toward the proximal end with respect to the stent;

wherein the releasing comprises releasing the fixed state between the thread and the protrusion by breaking the protrusion due to a force for moving the inner shaft toward the proximal end with respect to the stent.

7. A stent delivery method comprising:

inserting, from a first lumen into a second lumen together with an inner shaft that has a longitudinal axis and a tubular outer sheath through which the inner shaft is inserted so as to be movable in the direction along the longitudinal axis, a stent having a distal end and a proximal end, in such a state that the stent in a radially contracted form is held in a cylindrical gap between the inner shaft and the outer sheath and that a distal-end section of the stent is fixed to the inner shaft by fixing a thread that is attached to the distal-end section of the stent to the inner shaft;

exposing the entire stent from the outer sheath, while maintaining the state in which the distal-end section of the stent is fixed to the inner shaft, by moving the outer sheath toward the proximal end with respect to the inner shaft and the stent; and releasing the fixed state between the distal-end section of the stent and the inner shaft by cutting the thread before the inner shaft is moved toward the proximal end with respect to the stent.

8. A stent delivery method comprising:

inserting, from a first lumen into a second lumen together with an inner shaft that has a longitudinal axis and a tubular outer sheath through which the inner shaft is inserted so as to be movable in the direction along the longitudinal axis, a stent having a distal end and a proximal end, in such a state that the stent in a radially contracted form is held in a cylindrical gap between the inner shaft and the outer sheath and that a distal-end section of the stent is fixed to the inner shaft by fixing a thread that is attached to the distal-end section of the stent to the inner shaft by hooking the thread on a protrusion that is provided on the inner shaft and at least a section of the protrusion extends in the direction from a proximal end of the inner shaft toward a distal end thereof, the inner shaft has, at the distal-end section of the inner shaft, a through-hole that penetrates a tube wall thereof in a radial direction and the protrusion extends from a proximal end of the periphery of the through-hole toward the distal end of the inner shaft;

exposing the entire stent from the outer sheath, while maintaining the state in which the distal-end section of the stent is fixed to the inner shaft, by moving the outer sheath toward the proximal end with respect to the inner shaft and the stent; and releasing the fixed state between the distal-end section of the stent and the inner shaft by moving the inner shaft toward the proximal end with respect to the stent.

* * * * *